(12) United States Patent
Forsell

(10) Patent No.: US 6,454,699 B1
(45) Date of Patent: *Sep. 24, 2002

(54) FOOD INTAKE RESTRICTION WITH CONTROLLED WIRELESS ENERGY SUPPLY

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,775

(22) Filed: Feb. 11, 2000

(51) Int. Cl.⁷ .................................................. A61F 2/04
(52) U.S. Cl. ...................................... 600/30; 623/23.65
(58) Field of Search ................................... 128/897–899; 600/29–32, 37, 593; 604/27–28; 606/139–141, 151, 157, 201–203, 213, 228; 607/41; 623/23.65, 23.67

(56) References Cited

U.S. PATENT DOCUMENTS

| | | | | |
|---|---|---|---|---|
| 3,750,194 A | * | 8/1973 | Summers | 600/31 X |
| 3,875,928 A | * | 4/1975 | Angelchik | 600/37 |
| 4,246,893 A | * | 1/1981 | Berson | 128/898 |
| 4,592,355 A | * | 6/1986 | Antebi | 606/144 |
| 4,696,288 A | * | 9/1987 | Kuzmak et al. | 128/898 |
| 5,042,084 A | | 8/1991 | Daly | |
| 5,074,868 A | * | 12/1991 | Kuzmak | 606/157 |
| 5,160,338 A | * | 11/1992 | Vincent | 606/157 |
| 5,226,429 A | * | 7/1993 | Kuzmak | 128/898 |
| 5,449,368 A | * | 9/1995 | Kuzmak | 606/157 |
| 5,509,888 A | * | 4/1996 | Miller | 600/29 |
| 5,704,893 A | * | 1/1998 | Timm | 600/29 |
| 5,769,877 A | * | 6/1998 | Barreras | 607/61 |
| 5,910,149 A | * | 6/1999 | Kuzmak | 606/157 |
| 5,938,669 A | * | 8/1999 | Klaiber et al. | 606/157 |
| 5,978,712 A | * | 11/1999 | Suda et al. | 607/41 |
| 6,074,341 A | * | 6/2000 | Anderson et al. | 600/29 |

FOREIGN PATENT DOCUMENTS

| | | |
|---|---|---|
| WO | WO 00/09048 | 2/2000 |
| WO | WO 00/15158 A1 | 3/2000 |
| WO | WO 01/12078 | 8/2000 |

* cited by examiner

Primary Examiner—Kevin Shaver
Assistant Examiner—Joseph A. Cadugan
(74) Attorney, Agent, or Firm—Nixon & Vanderhye, P.C.

(57) ABSTRACT

A food intake restriction apparatus and method includes and uses an operable restriction device implanted in a patient and engaging the stomach or esophagus to form an upper pouch and a restricted stoma opening in the stomach or esophagus. A source of energy external to the patient's body and a control device for releasing wireless energy from the source of energy from outside the patient's body are provided. The released wireless energy is used in connection with the operation of the restriction device, to enlarge it to allow food passage, or to contract it to substantially prevent food passage.

145 Claims, 7 Drawing Sheets

FOOD INTAKE RESTRICTION WITH CONTROLLED WIRELESS ENERGY SUPPLY

BACKGROUND OF THE INVENTION

The present invention relates to a food intake restriction apparatus and method. More specifically, the invention relates to a food intake restriction apparatus and method for surgical application in the abdomen of a patient for forming an upper pouch of the stomach and a restricted stoma opening in the stomach or esophagus. The term patient includes an animal or a human being.

Food intake restriction apparatus in the form of a gastric banding device, in which a band encircles a portion of a patient's stomach to restrict the food intake of the patient, have been used in surgery for morbid obesity to form a small gastric pouch above the band and a reduced stoma opening in the stomach. Although such a band is applied around the stomach to obtain an optimal stoma opening during surgery, some prior gastric banding devices are provided with an adjustment means enabling a minor post-operation adjustment of the size of the stoma opening. In all such prior art devices such as disclosed in U.S. Pat. No. 4,592,339, European Patent No. 0611561 and International Patent Application WO 94/27504, the adjustment means typically comprises an inflatable cavity in the band and an injection port in fluid connection with the inflatable cavity for adding fluid to or withdrawing fluid from the latter. In practice, the band is made of silicone rubber which is a material approved for implantation and the fluid is a liquid such as an isotonic salt solution.

It has also been found that the volume of the gastric pouch above the band increases in size up to ten times after operation. Therefore the pouch volume during surgery needs to be very small, approximately 7 ml. To enable the patient to feed the stomach with sufficient nutrition immediately after an operation considering such a small gastric pouch, the stoma initially needs to be relatively large and later needs to be substantially reduced, as the pouch volume increases. To be able to achieve a significant range of adjustment of the band, the cavity in the band has to be relatively large and is defined by a thin flexible wall, normally made of silicone material. Furthermore, the size of the stoma opening has to be gradually reduced during the first year after surgery as the gastric pouch increases in size. As indicated above, the reduction of the stoma opening using the prior art devices is achieved by adding liquid to the cavity of the band via the injection port to expand the band radially inwardly.

A great disadvantage of repeatedly injecting liquid via the injection port is the increased risk of the patient getting an infection in the body area surrounding the injection port. If such an infection occurs the injection port has to be surgically removed from the patient. Moreover, such an infection might be spread along the tube interconnecting the injection port and the band to the stomach, causing even more serious complications. Thus, the stomach might be infected where it is in contact with the band, which might result in the band migrating through the wall of the stomach. Also, it is uncomfortable for the patient when the necessary, often many, post-operation adjustments of the stoma opening are carried out using an injection needle penetrating the skin of the patient into the injection port.

It may happen that the patient swallows pieces of food too large to pass through the restricted stoma opening. If that occurs the patient has to visit a doctor who can remove the food pieces, if the band design so permits, by withdrawing some liquid from the band to enlarge the stoma opening to allow the food pieces to pass the stoma. Then, the doctor has to add liquid to the band in order to regain the restricted stoma opening. Again, these measures require the use of an injection needle penetrating the skin of the patient, which is uncomfortable for the patient.

SUMMARY OF THE INVENTION

An object of the invention is to provide a food intake restriction apparatus for forming a stoma opening in the stomach or esophagus of a patient which permits regular post-operation adjustments that are comfortable for the patient.

Another object of the present invention is to provide a food intake restriction apparatus which is easy to adjust and does not require the use of an injection needle for accomplishing post-operation adjustments of the stoma opening.

Accordingly, there is provided a food intake restriction apparatus, comprising an operable restriction device implanted in a patient and engaging the stomach or esophagus to form an upper pouch of the stomach and a stoma opening in the stomach or esophagus, a source of energy external to the patient's body, and a control device for releasing wireless energy from the external source of energy, wherein the released wireless energy is used in connection with the operation of the restriction device.

As a result, the advantage is achieved that the implanted restriction device can be non-invasively adjusted by the control device. Furthermore, the apparatus of the invention provides simple and effective control of the energy supplied to implanted components of the apparatus which ensures an extended and reliable functionality of the apparatus, possibly for the rest of the patient's natural life, and at lest many years.

The restriction device preferably controls the cross-sectional area of the food passageway in the stomach or esophagus. As a result, the patient may be allowed to use the control device to temporarily enlarge the stoma opening to remove food pieces stuck therein.

Preferably the control device also controls the restriction device. The control device may comprise an internal control unit, preferably including a microprocessor, implanted in the patient for controlling the restriction device. The control device may further comprise an external control unit outside the patient's body, wherein the internal control unit is programmable by the external control unit, for example for controlling the restriction device over time. Alternatively, the internal control unit may control the restriction device over time in accordance with an activity schedule program, which may be adapted to the patient's needs.

Conveniently, the external control unit may load the internal control unit with data in accordance with a loading mode only authorized for a doctor. For specialized controls of the restriction device, the external control unit may control the internal control unit in accordance with a doctor mode, only authorized for the doctor. For simple controls of the restriction device, the external control unit may control the internal control unit in accordance with a patient mode permitted for the patient. Thus, by using the external control unit in accordance with different modes it is possible to have certains functions of the restriction device controlled by the patient and other more advanced functions controlled by the doctor, which enables a flexible post-operation treatment of the patient.

Generally, the apparatus further comprises an operation device implanted in the patient for operating the restriction device, wherein the control device controls the operation device to operate the restriction device.

The operation device may comprise hydraulic means and at least one valve for controlling a fluid flow in the hydraulic means. The control device may suitably comprise a wireless remote control for controlling the valve. The restriction device may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the wireless energy isdirectly used for operation of the restriction device, i.e. the restriction device is operated as the wireless energy is released from the external source of energy by the control device. The term "directly" is used to mean, on one hand, that the restriction device is promptly operated by using the released energy whithout first storing the latter, on the other hand, that the released energy may be somewhat delayed, in the order of seconds, by for instance an energy stabilizer before being used for the operation of the restriction device. As a result, a very simple control of the restriction device is achieved and there are only a few implanted components of the apparatus. For example, there is no implanted source of energy, such as a battery, nor any implanted complicated signal control system. This gives the advantage that the apparatus will be extremely reliable.

The wireless energy may be used for direct operation of the restriction device in a non-magnetic and/or non-mechanical manner.

Generally, the control device controls and directly or indirectly powers the operation device with wireless energy released from the source of energy and/or powers other implanted energy consuming components of the apparatus.

In a first particular embodiment in accordance with the first main aspect of the invention, the operation device comprises a motor, preferably an electric motor which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first main aspect of the invention, the control device is adapted to shift polarity of the polarized energy to reverse the operation device. The operation device maysuitably comprise an electric motor and the released energy may comprise electric energy.

In a third particular embodiment in accordance with the first main aspect of the invention, the restriction device is operable to perform a reversiblefunction. Such a reversing functionpreferably involves enlarging and restricting the food passageway by the restriction device, suitably in a stepless manner. There is a reversing device implanted in the patient for reversing the function performed by the restriction device. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gear box.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first main aspect of the invention, the restriction device comprises hydraulic means, for example including an expansible/contractible cavity for fluid. The operation device preferably comprises a pump for pumping a fluid in the hydraulic means, a motor for driving the pump, a valveless fluid conduit between the pump and the hydraulic means of the restriction device, and a reservoir for fluid, wherein the reservoir forms part of the conduit.All of the hydraulic components involved are preferably devoid of any non-return valve. This is of great advantage, because with valves involved there is always a risk of malfunction due to inproperly working valves, especially when long time periods passes between valve operations. The reservoir may form a fluid chamber with a variable volume, and the pump may distribute fluid from the chamber to the hydraulic means of the restriction device by reduction of the volume of the chamber and withdraw fluid from the hydraulic means to the chamber by expansion of the volume of the chamber.

In accordance with a second main aspect of the invention, the apparatus comprises a switch implanted in the patient for directly or indirectly switching the operation of the restriction device and an internal source of energy, such as a battery, implanted in the patient for supplying energy for the operation of the restriction device, wherein the switch directly or indirectly affects the supply of energy from the internal source of energy. This solution is advantageous for embodiments of the apparatus that have a relatively high energy consumption which cannot be met by direct supply of wireless energy.

In a first particular embodiment in accordance with the second main aspect of the invention, the switch switches between an off mode, in which the internal source of energy is not in use, and an on mode, in which the internal source of energy supplies energy for the operation of the restriction device. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted source of energy, such as a battery, can be significantly prolonged, since the implanted source of energy does not supply energy when the switch is in its off mode.

In a second particular embodiment in accordance with the second main aspect of the invention, the control device comprises a wireless remote control for controlling the internal source of energy. In this case, the switch is operable by the wireless energy from the external source of energy to switch between an off mode, in which the internal source of energy and remote control are not in use, and a standby mode, in which the remote control is permitted to control the internal source of energy to supply energy for the operation of the restriction device.

In a third particular embodiment in accordance with the second main aspect of the invention, the apparatus further comprises an energy transfer device implanted in the patient for transferring the wireless energy into storable energy, wherein the internal source of energy is capable of storing the storable energy. The internal source of energy preferably comprises an electric accumulator, at least one capacitor or at least one recharge able battery, or a combination of at least one capacitor and at least one recharge able battery. In this case, the switch switches from an off mode, in which the internal source of energy is not in use, to an on mode, in which the internal source of energy supplies energy for the operation of the restriction device.

The control device, preferably comprising a wireless remote control, may control the switch to switch between the on and off modes.

Alternatively, in this third particular embodiment an energy storage device may be implanted in the patient for storing the storable energy instead of the internal source of energy, wherein the switch is operable by energy from the implanted energy storage device to switch between an off mode, in which the internal source of energy is not in use, and an on mode, in which the internal source of energy supplies energy for the operation of the restriction device. In this case, the control device (the wireless remote control) controls the energy storage device to operate the switch.

The internal source of energy preferably comprises an electric source of energy, such as an accumulator or a battery having a life-time of at least 10 years. However, other kinds of sources are also conceivable, such as a nuclear source of energy or a chemical source of energy.

The above first, second and third and fourth particular embodiments described in connection with the first main aspect of the invention are also applicable in accordance with the second main aspect of the invention, i.e. where the apparatus comprises an implanted switch.

All of the above embodiments may be combined with at least one implanted sensor for sensing at least one physical parameter of the patient, wherein the control device may control the restriction device in response to signals from the sensor. For example, the sensor may comprise a pressure sensor for directly or indirectly sensing the pressure against the restriction device, human tissue or in the food passageway. The expression "indirectly sensing the pressure in the food passageway" should be understood to encompass the cases where the sensor senses the pressure against the restriction device or human tissue of the patient. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor. Where the control device comprises an internal control unit implanted in the patient, the internal control unit may suitably directly control the restriction device in response to signals from the sensor. In response to signals from the sensor, for example pressure, the patient's position or any other important physical parameter, the internal control unit may send information thereon to outside the patient's body. The control unit may also automatically control the restriction device in response to signals from the sensor. The control device may control the restriction device in response to from the pressure sensor.

For example, the control unit may control the restriction device to further restrict the stoma opening in the stomach in response to the sensor sensing that the patient is lying, or enlarge the stoma opening in response to the sensor sensing an abnormally high pressure against the restriction device.

Where the control device comprises an external control unit outside the patient's body, the external control unit may, suitably directly, control the restriction device in response to sensings by the sensor. The external control unit may store information on the physical parameter sensed by the sensor and may be manually operated to control the restriction device based on the stored information. In addition, there may be at least one implanted sender for sending information on the physical parameter sensed by the sensor.

An external data communicator may be provided outside the patient's body and an internal data communicator may be implanted in the patient for communicating with the external communicator. The implanted communicator may feed data related to the patient, or related to the implanted restriction device, back to the external communicator. Alternatively or in combination, the external communicator may feed data to the internal communicator. The implanted communicator may suitably feed data related to at least one physical signal of the patient.

Generally, the restriction device may control the size of the stoma opening in the stomach or esophagus. For example, the restriction device may be operable to open and close the food passageway or may steplessly control the cross-sectional area of the food passageway. The restriction device may be non-inflatable, i.e. with no hydraulic fluid involved for the adjustments of the restriction device. This eliminates problems with fluid leaking from the restriction device.

The apparatus may comprise an implanted energy transfer device, wherein the control device releases electric energy and the energy transfer device transfers the electric energy into kinetic energy for, preferably direct, operation of the restriction device. Suitably, an implanted stabilizer, such as a capacitor or a rechargeable accumulator, or the like, may be provided for stabilizing the electric energy released by the control device.

The control device may release energy for a determined time period or in a determined number of energy pulses. All of the above embodiments are preferably remote controlled. Thus, the control device advantageously comprises a wireless remote control transmitting at least one wireless control signal for controlling the restriction device. With such a remote control it will be possible to adapt the function of the apparatus to the patient's need over a period of time, which is beneficial with respect to the treatment of the patient.

The wireless remote control may be capable of obtaining information on the condition of the implanted restriction device and of controlling the restriction device in response to the information. Also, The remote control may be capable of sending information related to the restriction device from inside the patient'spatient?s body to the outside thereof.

In a particular embodiment of the invention, the wireless remote control comprises at least one external signal transmitter or tranceiver and at least one internal signal receiver or transciever implanted in the patient. In another particular embodiment of the invention, the wireless remote control comprises at least one external signal reciever or transceiver and at least one internal signal transmitter or transceiver implanted in the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

According to another aspect of the present invention there is provided a method of treating a human or animal suffering from morbid obesity, comprising: (a) Surgically implanting in the human or animal an operable restriction device engaging the human's or animal's stomach or esophagus to form an upper pouch of the stomach and a restricted stoma opening in the stomach or esophagus. (b) Providing a source of energy external to the patient's body. (c) Controlling the external source of energy from outside the patient's body to release wireless energy. And (d) using the released wireless energy in connection with the operation of the restriction device.

The method may further comprise (e) implanting in the human or animal an operation device which can adjust the restricted food passageway in response to supplied energy, and (f) using the released wireless energy to activate the implanted operation device to adjust the restricted stoma opening.

In the method: (f) may be practiced several times during the first year after the operation.

In accordance with yet another asdpect of the invention, there is provided a method of treating a human or animal suffering from morbid obesity, comprising the steps of placing at least two laparascopical trocars in the human's or animal's, inserting a dissecting tool through the trocars and dissecting an area of the stomach or esophagus, placing an operable restriction device in the dissected area, so that the restriction device engages the stomach or the esophagus to form a restricted stoma opening in the stomach or esophagus, providing a source of energy outside the human's or animal's body, controlling the external source of energy from outside the human's or animal's body to release wireless energy, and using the released wireless energy in connection with the operation of the restriction device.

In accordance with another alternative method, there is provided a method of treating a human or animal suffering from morbid obesity, comprising the steps of placing at least two laparascopical trocars in the human's or animal's body, inserting a dissecting tool through the trocars and dissecting an area of the stomach or esophagus, implanting an operable restriction device in the dissected area in engagement with the stomach or esophagus to form a restricted stoma opening in the stomach or esophagus, implanting an energy transfer device, providing an external source of energy, controlling the external source of energy to release wireless energy, and transferring the wireless energy by the energy transfer device into energy different than the wireless energy for use in connection with the operation of the restriction device. This method may further comprise implanting a stabilizer in the human or animal for stabilizing the energy transferred by the energy transfer device.

It is the primary object of the present invention to provide a simple yet effective method and apparatus for treating humans or animals that suffer's from morbid obesity. This and other objects of the invention will become clear from an inspection of the detailed description of the invention and from the appended claims.

DETAILED DESCRIPTION OF THE DRAWINGS

Figure 1:
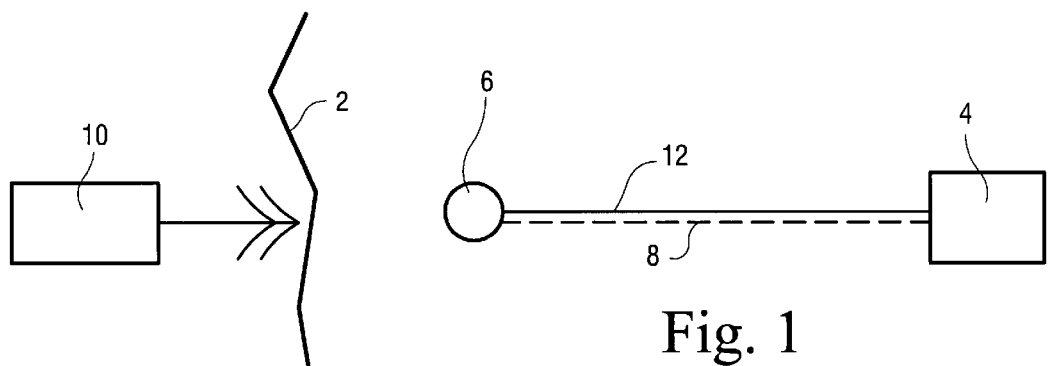
FIGS. 1 to 5 are schematic block diagrams illustrating five embodiments, respectively, of the invention, in which wireless energy released from an external source of energy is used for direct operation of a restriction device engaging the stomach or esophagus of a patient.

FIG. 1 schematically shows an embodiment of the food intake restriction apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body.

The apparatus of FIG. 1 comprises an implanted operable restriction device 4, which engages the patient's stomach esophagus to form a restricted stoma opening in the stomach. The restriction device 4 is capable of performing a reversible function, i.e. to enlarge and reduce the size of the stoma opening. An implanted control unit 6 controls the restriction device 4 via a control line 8 to form an adequate size of the stoma opening. An external control unit 10 includes an external source of energy and a wireless remote control transmitting a control signal generated by the external source of energy. The control signal is received by a signal receiver incorporated in the implanted control unit 6, whereby the control unit 6 controls the implanted restriction device 4 in response to the control signal. The implanted control unit 6 also uses energy from the control signal for directly operating the restriction device 4 via a power supply line 12, as the control signal is transmitted.

Figure 2:
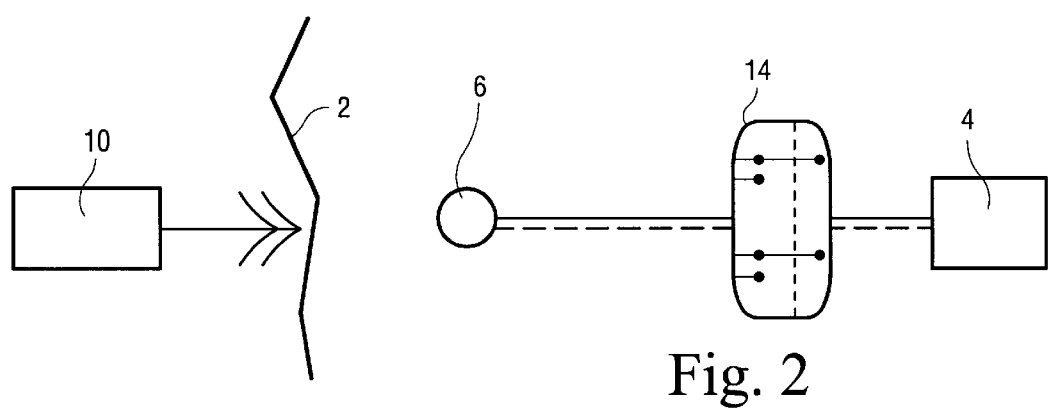

FIG. 2 shows an embodiment of the invention identical to that of FIG. 1, except that a reversing device in the form of a switch 14 also is implanted in the patient for reversing the restriction device 4. The control unit 6 uses the switch 14 to reverse the function performed by the restriction device 4, i.e. enlarging and restricting the stoma opening. More precisely, the external control unit 10 releases energy carried by a wireless signal and the implanted control unit 6 transfers the wireless energy into a current for operating the switch 14. When the control unit 6 shifts the polarity of the current the switch 14 reverses the function performed by the restriction device 4.

Figure 3:
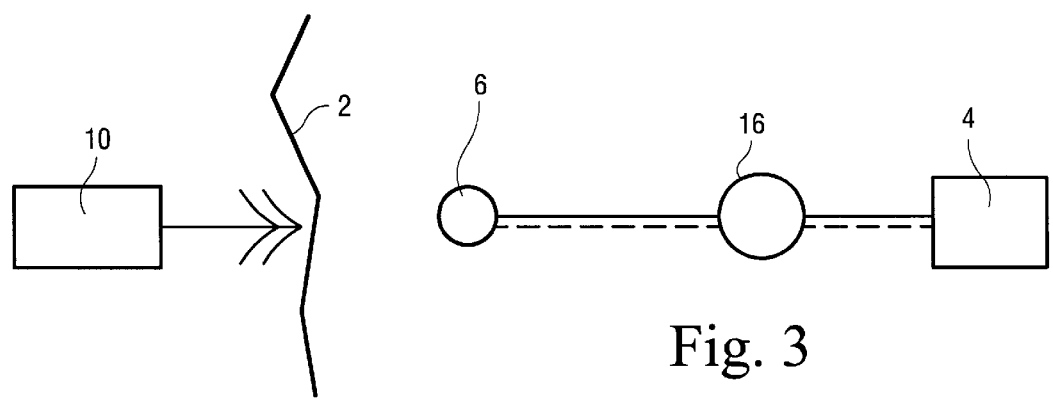

FIG. 3 shows an embodiment of the invention identical to that of FIG. 1, except that an operation device in the form of a motor 16 also is implanted in the patient. The implanted control unit 6 powers the motor 16 with wireless energy released from the external source of energy of the external control unit 10. The implanted control unit 6 controls the operation of the motor 16 in response to a control signal from the remote control of the external control unit 10.

Figure 4:
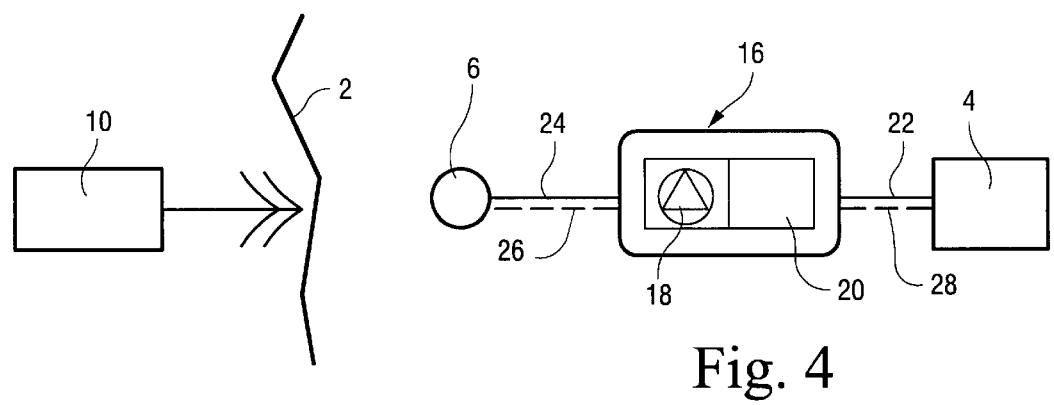

FIG. 4 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to reduce the size of the stoma opening, and hydraulic fluid is pumped by the motor/pump unit 18 back from the restriction device 4 to the reservoir 20 to enlarge the size of the stoma opening. The external control unit 10 releases energy carried by a wireless signal and the implanted control unit 6 transfers the wireless energy into a current, for example a polarized current, for powering the motor/pump unit 18 via an electric power supply line 24. The implanted control unit 6 controls the motor/pump unit 16 and the restriction device 4 via control lines 26 and 28.

Figure 5:
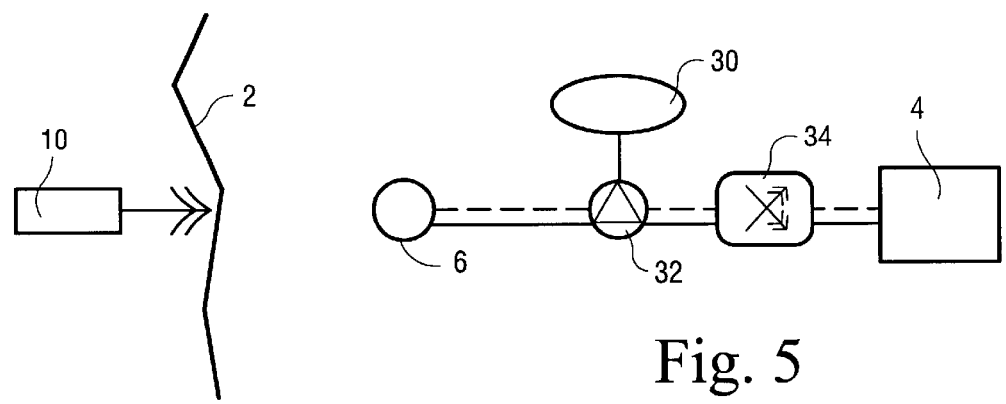

FIG. 5 shows an embodiment of the invention comprising the restriction device 4, hydraulically operated, and the implanted control unit 6, and further comprising a hydraulic fluid reservoir 30, a motor/pump unit 32 and a reversing device in the form of a hydraulic valve shifting device 34, all of which are implanted in the patient. The motor of the motor/pump unit 32 is an electric motor.

In response to a control signal from the wireless remote control of the external control unit 10 the implanted control unit 6 unit 6 to switch between an off mode, in which the implanted source of energy 36 is not in use, and an on mode, in which the implanted source of energy 36 supplies energy for the operation of the restriction device 4.

In response to a control signal from the external control unit 40 the implanted control unit 6 powers the motor/pump unit 36 with energy from the battery 32, whereby the motor/pump unit 36 distributes hydraulic fluid between the reservoir 34 and the restriction device 4. The control unit 6 controls the shifting device 38 to shift the hydraulic fluid flow direction between one direction in which the fluid is pumped by the motor/pump unit 36 from the reservoir 34 to the restriction device 4 to reduce the size of the stoma opening, and another opposite direction in which the fluid is pumped by the motor/pump unit 36 back from the restriction device 4 to the reservoir 34 to enlarge the size of the stoma opening.

Figure 6:
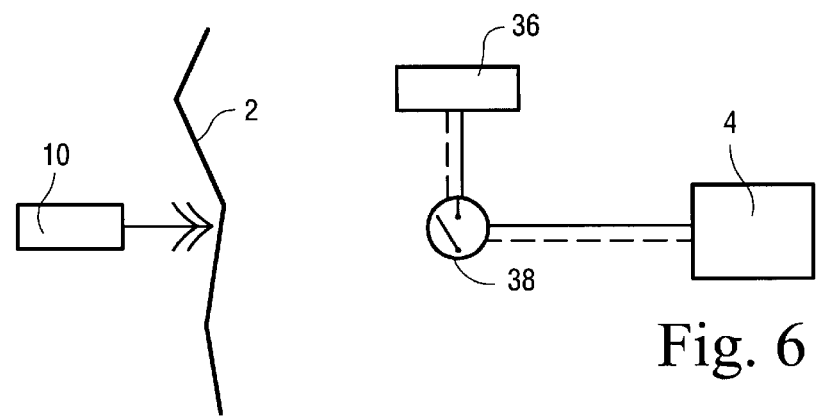
FIGS. 6 to 10 are schematic block diagrams illustrating five embodiments, respectively, of the invention, in which a switch is implanted in the patient for directly or indirectly switching the operation of the restriction device.

FIG. 6 shows an embodiment of the invention identical to that of FIG. 4, except that a battery 42 is substituted for the accumulator 28, the external control unit 40 of the embodiment of FIG. 5 is substituted for the external control unit 10 and an electric motor 44 is implanted in the patient for operating the restriction device 4. In response to a control signal from the external control unit 40 the implanted control unit 6 powers the motor 44 with energy from the battery 42, whereby the motor 44 operates the restriction device 4.

Figure 7:
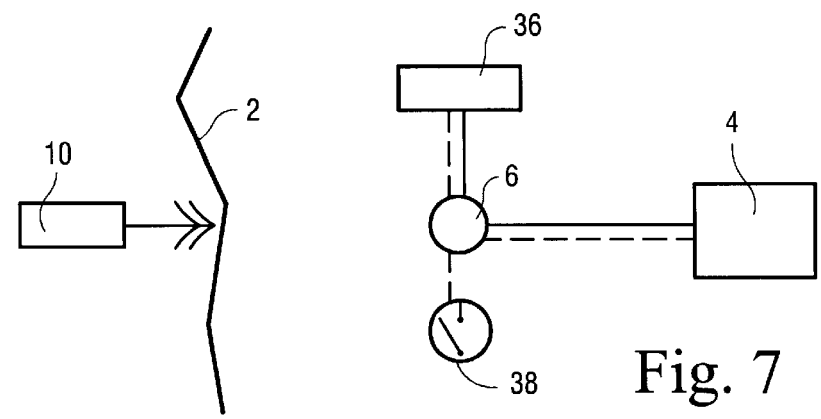

FIG. 7 shows an embodiment of the invention identical to that of FIG. 6, except that also the control unit 6 is implanted, in order to receive a control signal from the wireless remote control of the external control unit 10. The switch 38 is operated by the wireless energy from the external source of energy 10 to switch between an off mode, in which the implanted source of energy 36 and the wireless remote control of the external control unit 10 are not in use, i.e. the control unit 6 is not capable of receiving the control signal, and a standby mode, in which the wireless remote control is permitted to control the internal source of energy 36, via the implanted control unit 6, to supply energy for the operation of the restriction device 4.

Figure 8:
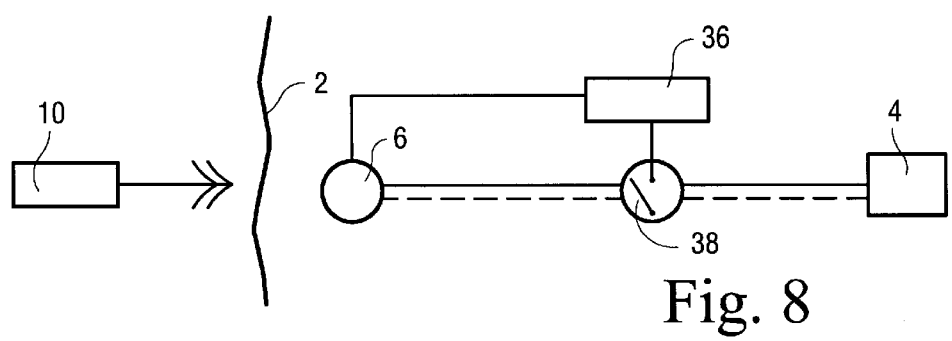

FIG. 8 shows an embodiment of the invention identical to that of FIG. 7, except that an energy transfer device for transferring the wireless energy into storable energy is incorporated in the implanted control unit 6 and that the implanted source of energy 36 is of a type that is capable of storing the storable energy. In this case, in response to a control signal from the external control unit 10, the implanted control unit 6 controls the switch 38 to switch from an off mode, in which the implanted source of energy 36 is not in use, to an on mode, in which the source of energy 36 supplies energy for the operation of the restriction device 4.

Figure 9:
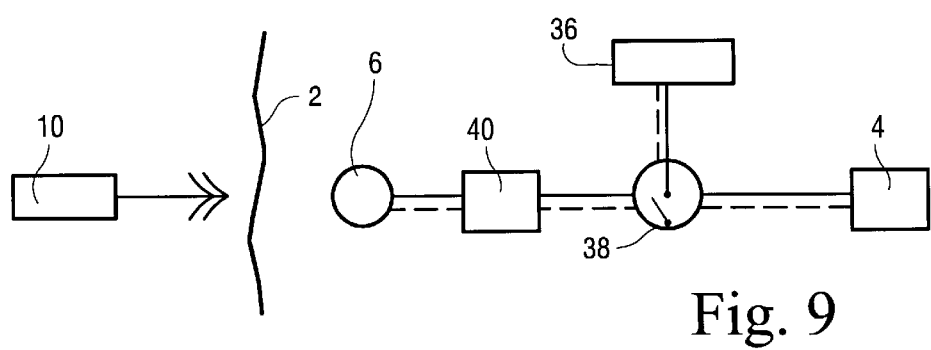

FIG. 9 shows an embodiment of the invention identical to that of FIG. 8, except that an energy storage device 40 also is implanted in the patient for storing the storable energy transferred from the wireless energy by the transfer device of the control unit 6. In this case, the implanted control unit 6 controls the energy storage device 40 to operate the switch 38 to switch between an off mode, in which the implanted source of energy 36 is not in use, and an on mode, in which the implanted source of energy 36 supplies energy for the operation of the restriction device 4.

Figure 10:
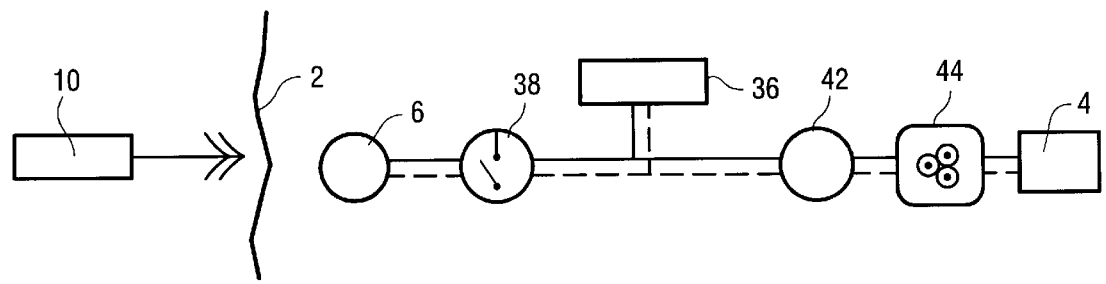

FIG. 10 shows an embodiment of the invention identical to that of FIG. 8, except that a motor 42 and a mechanical reversing device in the form of a gear box 44 also are implanted in the patient. The implanted control unit 6 controls the gear box 44 to reverse the function performed by the restriction device 4 (mechanically operated), i.e. enlarging and restricting the food passageway.

Figure 11:
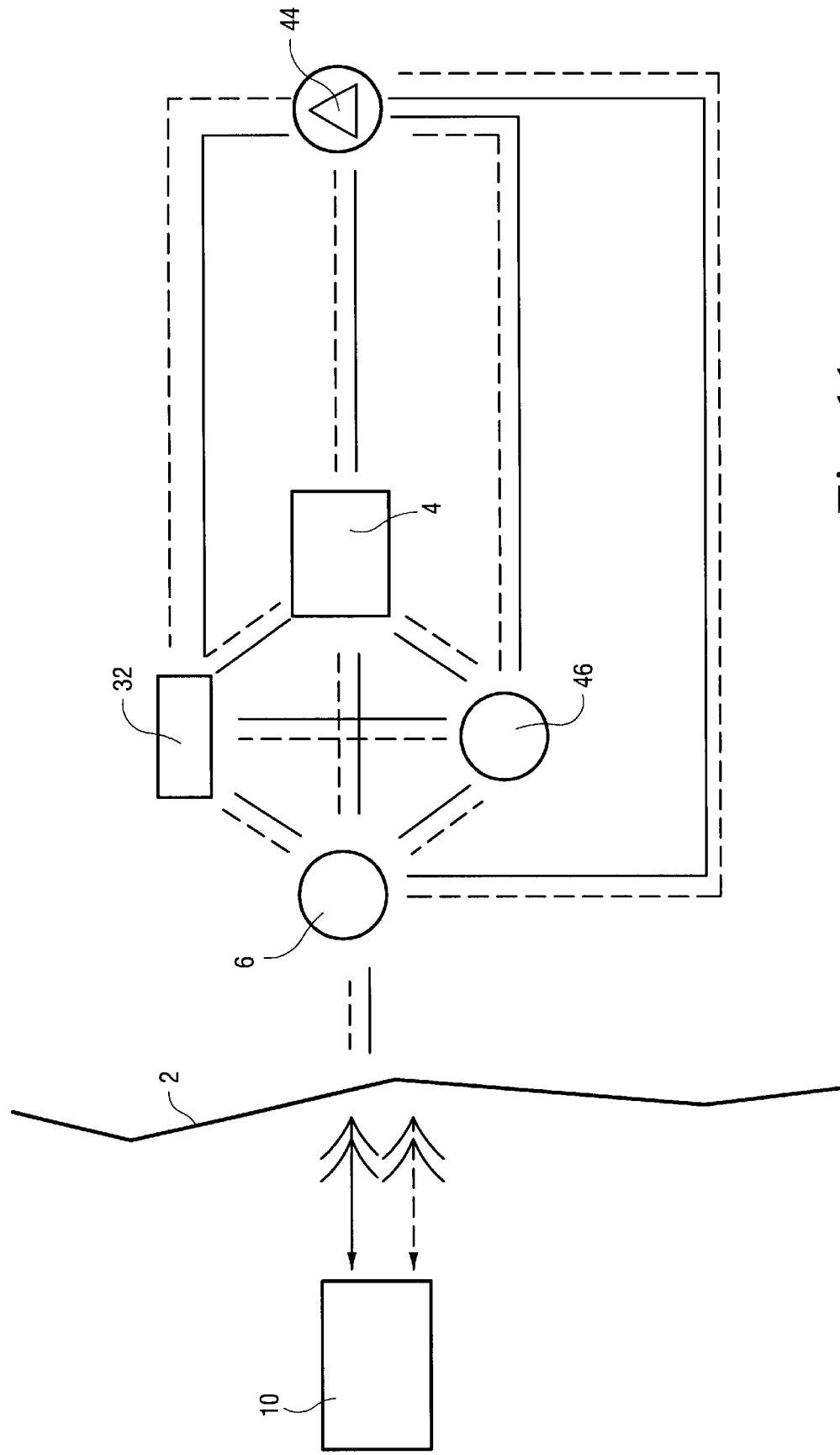
FIG. 11 is a schematic block diagram illustrating conceivable combinations of implanted components for achieving various communication options.

FIG. 11 schematically shows conceivable combinations of implanted components of the apparatus for achieving various communication options. Basically, there are the implanted restriction device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted restriction device 4 in response to the control signal.

A sensor 46 may be implanted in the patient for sensing a physical parameter of the patient, such as the pressure in the stomach. The control unit 6, or alternatively the external control unit 10, may control the restriction device 4 in response to signals from the sensor 46. A tranceiver may be combined with the sensor 46 for sending information on the sensed physical parameter to the external control unit 10. The wireless remote control of the external control unit 10 may comprise a signal transmitter or tranceiver and the implanted control unit 6 may comprise a signal receiver or transciever. Alternatively, the wireless remote control of the external control unit 10 may comprise a signal reciever or transceiver and the implanted control unit 6 may comprise a signal transmitter or transceiver. The above tranceivers, transmitters and receivers may be used for sending information or data related to the restriction device 4 from inside the patient's body to the outside thereof.

Those skilled in the art will realize that the above various embodiments according to FIGS. 1–11 could be combined in many different ways.

Figure 12:
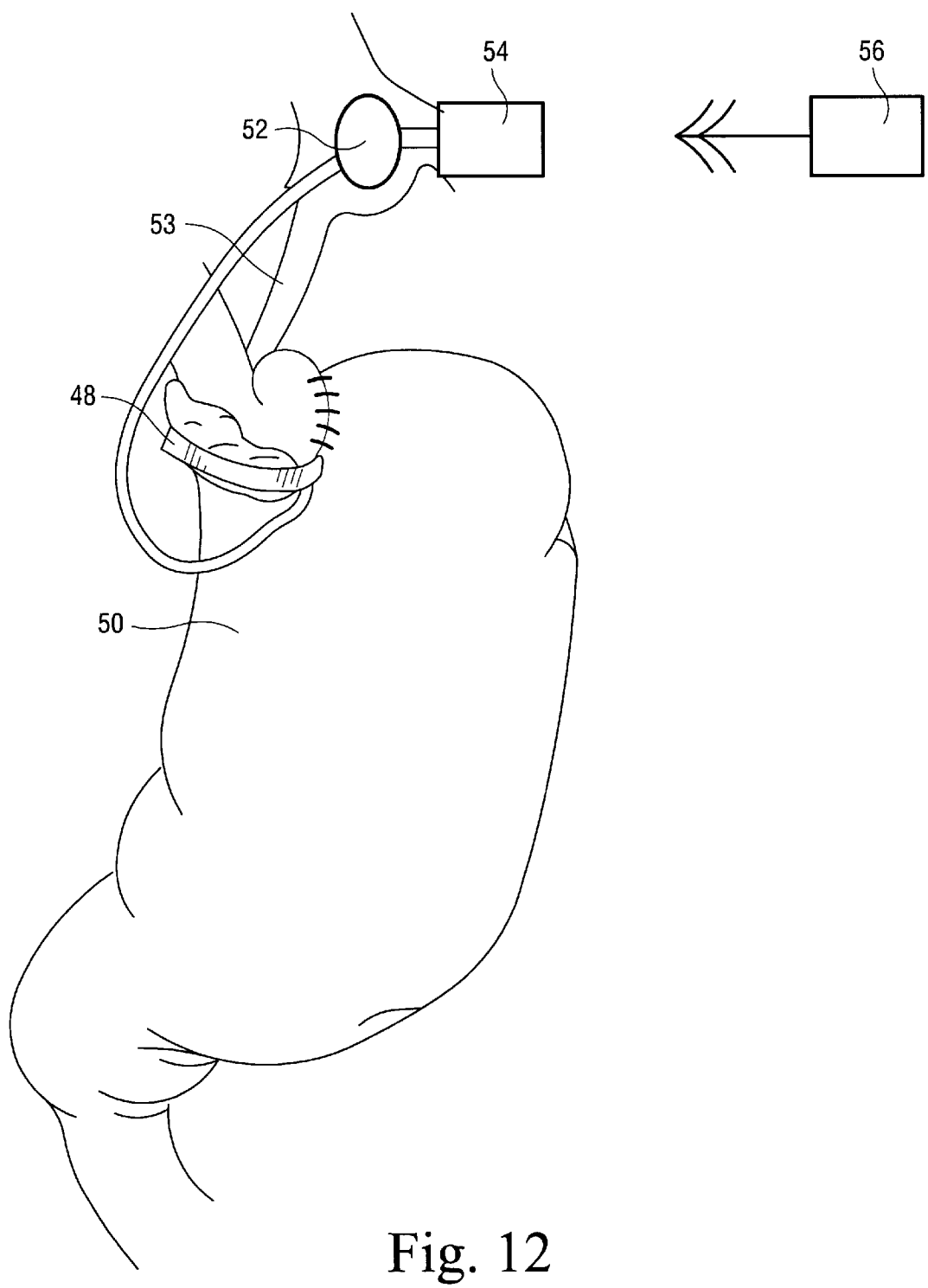
FIG. 12 illustrates the apparatus in accordance with the invention implanted in a patient.

FIG. 12 illustrates how any of the above-described embodiments of the food intake restriction apparatus of the invention may be implanted in a patient. Thus, the apparatus comprises a restriction device 48 implanted in the patient and engaging the stomach 50, and an operation device 52 for operating the restriction device 48. The restriction device 48 engages the stomach 50 and a portion of the stomach, thereby forming an upper pouch 53 of the stomach. A control device in the form of a wireless remote control comprises an implanted control unit 54, which includes a signal receiver, for controlling the operation device 52, and an external control unit 56 including a signal transmitter for transmitting a control signal to the signal receiver of the implanted control unit 54. The implanted control unit 54 is capable of transferring signal energy from the control signal into electric energy for powering the operation device 52 and for energizing electric energy consuming implanted components of the apparatus.

Figure 13:
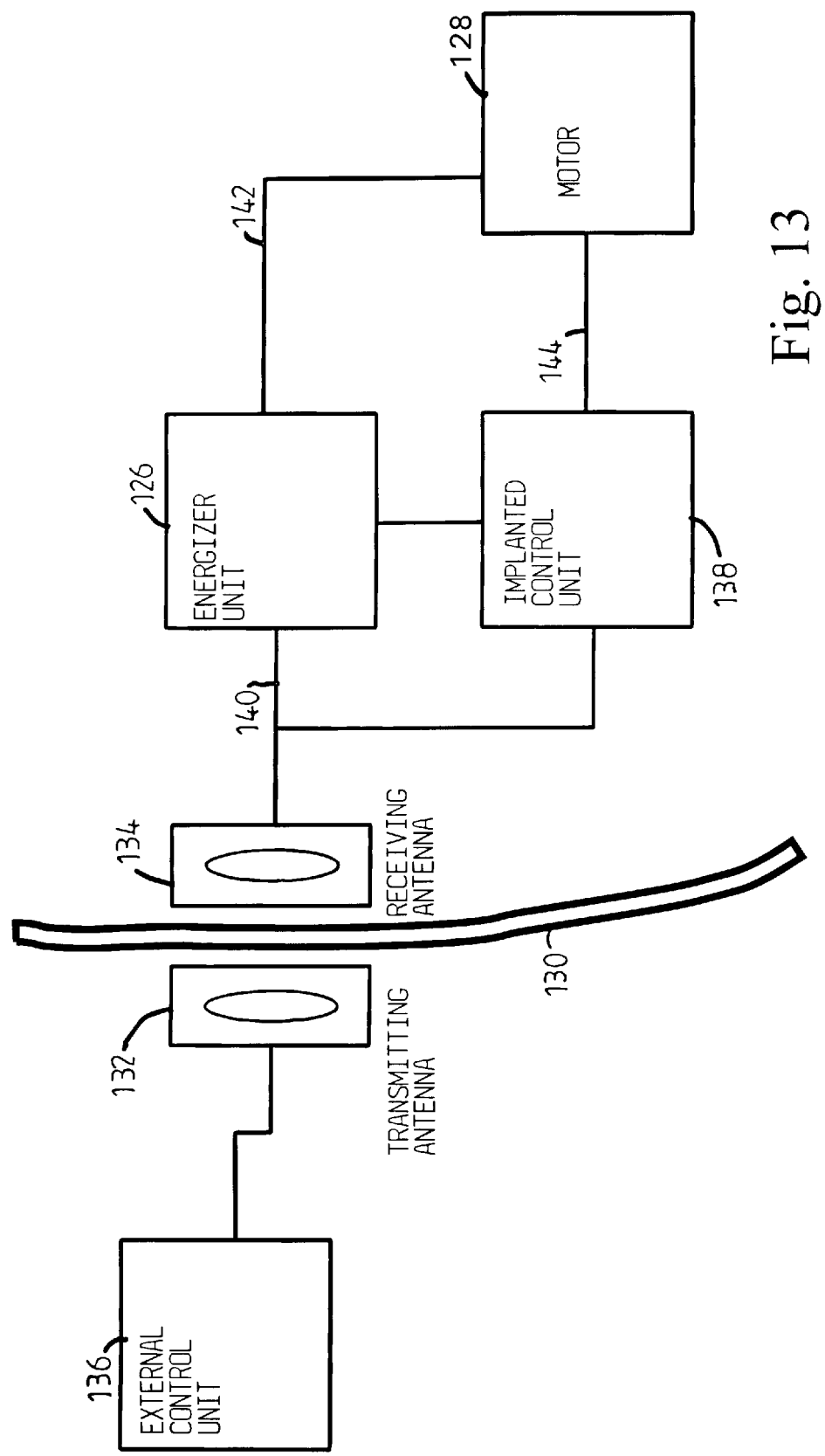
FIG. 13 is a block diagram illustrating remote control components of an embodiment of the invention.

FIG. 13 shows the basic parts of a wireless remote control of the apparatus of the invention including an electric motor 128 for operating a restriction device, for example of the type illustrated in FIG. 12. In this case, the wireless remote control is based on the transmission of electromagnetic wave signals, often of high frequencies in the order of 100 kHz–1 gHz, through the skin 130 of the patient. In FIG. 11, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the restriction device. The microprocessor starts a command by applying a high frequency signal on the antenna 132. After a short time, when the signal has energized the implanted parts of the control system, commands are sent to contract or enlarge the restriction device in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the restriction device depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect said battery to the control unit 138 in an on mode when said switch is powered by said power supply and to keep said battery disconnected from the control unit in a standby mode when said switch is unpowered.

Figure 14:
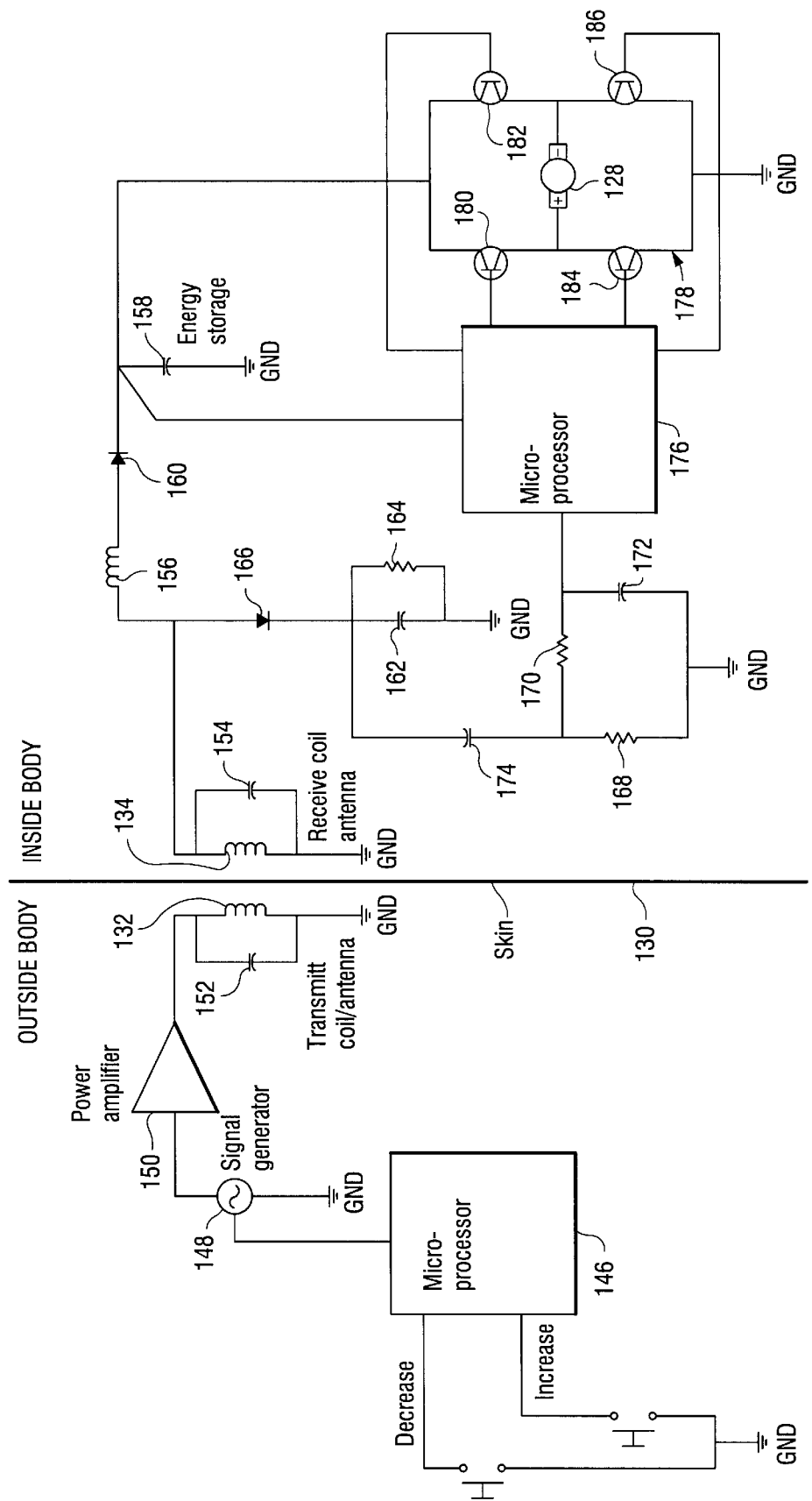
FIG. 14 is a schematic view of exemplary circuitry used for the components of the block diagram of FIG. 13.

With reference to FIG. 14, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168, 170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

What is claimed is:

1. A food intake restriction apparatus for an obese patient, comprising:
    an operable restriction device adapted to be implanted in the patient to engage the stomach or esophagus to form an upper pouch of the stomach and a restricted stoma opening in the stomach or esophagus,
    a source of energy external to the patient's body,
    a control device operable from outside the patient's body for releasing wireless energy from said source of energy for use in the operation of said restriction device to vary the restricted stoma opening, and
    an energy transfer device, adapted to be implanted in the patient, for transferring said wireless energy into a different form of energy useable by said operable restriction device.

2. The apparatus according to claim 1, wherein said control device controls said restriction device.

3. The apparatus according to claim 2, wherein said control device comprises an internal control unit adapted to be implanted in the patient for controlling said operation device.

4. The apparatus according to claim 3, wherein said internal control unit is programmable.

5. The apparatus according to claim 4, wherein said control device comprises an external control unit outside the patient's body, said internal control unit being programmable by said external control unit.

6. The apparatus according to claim 5, wherein said external control unit loads said internal control unit with data in accordance with a loading mode only authorized for a doctor.

7. The apparatus according to claim 5, wherein said external control unit controls said internal control unit in accordance with a doctor mode only authorized for a doctor.

8. The apparatus according to claim 5, wherein said external control unit controls said internal control unit in accordance with a patient mode permitted for the patient.

9. The apparatus according to claim 4, wherein said internal control unit is programmable for controlling said restriction device over time.

10. The apparatus according to claim 9, wherein said internal control unit controls said restriction device over time in accordance with an activity schedule program.

11. The apparatus according to claim 9, wherein said internal control unit comprises a microprocessor.

12. The apparatus according to claim 1, further comprising an operation device adapted to be implanted in the patient for operating said restriction device, wherein said control device controls said operation device to operate said restriction device.

13. The apparatus according to claim 12, wherein said operation device comprises hydraulic means and at least one valve for controlling a fluid flow in said hydraulic means.

14. The apparatus according to claim 13, wherein said control device comprises a wireless remote control for controlling said valve.

15. The apparatus according to claim 12, wherein said restriction device comprises hydraulic means and said operation device comprises a reservoir forming a fluid chamber with a variable volume connected to said hydraulic means, and said operation device distributes fluid from said chamber to said hydraulic means by reduction of the volume of said chamber and withdraws fluid from said hydraulic means to said chamber by expansion of the volume of said chamber.

16. The apparatus according to claim 1, wherein said wireless energy released from said external source of energy isdirectly used for operation of said restriction device.

17. The apparatus according to claim 16, wherein said wireless energy is directly used for operation of said restriction device in a non-magnetic manner.

18. The apparatus according to claim 17, wherein said motor comprises a hydraulic or pneumatic fluid motor, and said control device controls the fluid flow through said fluid motor.

19. The apparatus according to claim 16, wherein said wireless energy isdirectly used for operation of said restriction device in a non-mechanical manner.

20. The apparatus according to claim 16, further comprising an operation device for operating said restriction device, wherein said wireless energy directly or indirectly powers said operation device.

21. The apparatus according to claim 20, wherein said control device controls said operation device.

22. The apparatus according to claim 21, wherein said operation device comprises a motor.

23. The apparatus according to claim 22, wherein said motor comprises a rotary motor, and said control device controls said rotary motor to rotate a desired number of revolutions.

24. The apparatus according to claim 22, wherein said motor comprises a linear motor.

25. The apparatus according to claim 22, wherein said motor comprises an electric motor having electrically conductive parts made of plastics.

26. The apparatus according to claim 21, wherein said control device releases polarized energy from said source of energy.

27. The apparatus according to claim 26, wherein said operation device comprises an electric motor and said released energy comprises electric energy.

28. The apparatus according to claim 21, wherein said control device shifts polarity of said released energy to reverse said operation device.

29. The apparatus according to claim 21, wherein said restriction device is operable to perform a reversible function.

30. The apparatus according to claim 29, further comprising a reversing device implanted in the patient for reversing said function performed by said restriction device.

31. The apparatus according to claim 30, wherein said control device controls said reversing device to reverse said function performed by said restriction device.

32. The apparatus according to claim 30, wherein said reversing device comprises hydraulic means including a valve for shifting the flow direction of a fluid in said hydraulic means.

33. The apparatus according to claim 30, wherein said reversing device comprises a mechanical reversing device.

34. The apparatus according to claim 33, wherein said mechanical reversing device comprises a switch.

35. The apparatus according to claim 33, wherein said reversing device comprises a gear box.

36. The apparatus according to claim 30, wherein said reversing device comprises a switch.

37. The apparatus according to claim 36, wherein said switch is operated by said released energy.

38. The apparatus according to claim 37, wherein said control device controls the operation of said switch by shifting polarity of said released energy operating said switch.

39. The apparatus according to claim 37, wherein said switch comprises an electric switch and said source of energy supplies electric energy for the operation of said switch.

40. The apparatus according to claim 36, wherein said operation device comprises a motor, and said reversing device reverses said motor.

41. The apparatus according to claim 20, wherein said restriction device comprises hydraulic means and said operation device comprises a pump for pumping a fluid in said hydraulic means.

42. The apparatus according to claim 41, wherein said operation device comprises a motor for driving said pump.

43. The apparatus according to claim 42, wherein said operation device comprises a fluid conduit between said pump and said hydraulic means of said restriction device, and a reservoir for fluid, said reservoir forming part of said conduit.

44. The apparatus according to claim 43, wherein said hydraulic means, pump and conduit is devoid of any non-return valve.

45. The apparatus according to claim 44, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

46. The apparatus according to claim 16, further comprising an stabilizer adapted to be implanted in the patient for stabilizing the energy released by said control device.

47. The apparatus according to claim 46, wherein the energy released by said control device comprises electric energy and said stabilizer comprises at least one capacitor.

48. The apparatus according to claim 1, further comprising a switch adapted to be implanted in the patient for directly or indirectly switching the operation of said restriction device.

49. The apparatus according to claim 48, further comprising an internal source of energy adapted to be implanted in the patient for supplying energy for the operation of said restriction device, wherein said switch directly or indirectly affects the supply of energy from said internal source of energy.

50. The apparatus according to claim 49, wherein said switch switches between an "off" mode, in which said internal source of energy is not in use, and an "on" mode, in which said internal source of energy supplies energy for the operation of said restriction device.

51. The apparatus according to claim 50, wherein said switch is operable by said wireless energy released from said external source of energy.

52. The apparatus according to claim 51, wherein said control device controls said external source of energy to release said wireless energy.

53. The apparatus according to claim 52, wherein said control device comprises a wireless remote control.

54. The apparatus according to claim 49, wherein said control device comprises a wireless remote control for controlling said internal source of energy.

55. The apparatus according to claim 54, wherein said switch is operable by said wireless energy from said external source of energy to switch between an "off" mode, in which said internal source of energy and remote control are not in use, and a "standby" mode, in which said remote control is permitted to control said internal source of energy to supply energy for the operation of said restriction device.

56. The apparatus according to claim 49, wherein said energy transfer device transfers said wireless energy into storable energy, further comprising an energy storage device adapted to be implanted in the patient for storing said storable energy.

57. The apparatus according to claim 56, wherein said switch is operable by energy from said implanted energy storage device to switch between an "off" mode, in which said internal source of energy is not in use, and an "on" mode, in which said internal source of energy supplies energy for the operation of said restriction device.

58. The apparatus according to claim 57, wherein said control device controls said energy storage device to operate said switch.

59. The apparatus according to claim 58, wherein said control device comprises a wireless remote control.

60. The apparatus according to claim 50, wherein said internal source of energy comprises an electric source of energy.

61. The apparatus according to claim 60, wherein said electric source of energy comprises at least one accumulator, at least one capacitor or at least one rechargeable battery, or a combination of at least one capacitor and at least one rechargeable battery.

62. The apparatus according to claim 60, wherein said control device comprises a wireless remote control.

63. The apparatus according to claim 50, wherein said internal source of energy comprises a nuclear source of energy.

64. The apparatus according to claim 50, wherein said internal source of energy comprises a chemical source of energy.

65. The apparatus according to claim 49, wherein said energy transfer device transfers said wireless energy into storable energy, wherein said internal source of energy is capable of storing said storable energy.

66. The apparatus according to claim 65, wherein said switch switches from an "off" mode, in which said internal source of energy is not in use, to an "on" mode, in which said source of energy supplies energy for the operation of said restriction device.

67. The apparatus according to claim 66, wherein said control device controls said switch to switch between said "on" and "off" modes.

68. The apparatus according to claim 60, wherein said electric source of energy comprises an accumulator or a battery having a life-time of at least 10 years.

69. The apparatus according to claim 48, further comprising a powered operation device adapted to be implanted in the patient for operating said restriction device.

70. The apparatus according to claim 69, wherein said control device controls said operation device.

71. The apparatus according to claim 70, wherein said operation device comprises a motor.

72. The apparatus according to claim 71, wherein said motor comprises a rotary motor, and said control device controls said rotary motor to rotate a desired number of revolutions.

73. The apparatus according to claim 71, wherein said motor comprises a linear motor.

74. The apparatus according to claim 71, wherein said motor comprises a hydraulic or pneumatic fluid motor, and said control device controls said fluid motor.

75. The apparatus according to claim 71, wherein said motor comprises an electric motor having electrically conductive parts made of plastics.

76. The apparatus according to claim 71, wherein said operation device comprises an electric motor and said released energy comprises electric energy.

77. The apparatus according to claim 70, wherein said control device releases polarized energy from said external source of energy for powering said operation device.

78. The apparatus according to claim 70, wherein said control device shifts polarity of said released energy to reverse said operation device.

79. The apparatus according to claim 70, wherein said restriction device is operable to perform a reversible function.

80. The apparatus according to claim 77, further comprising a reversing device adapted to be implanted in the patient for reversing said function performed by said restriction device.

81. The apparatus according to claim 80, wherein said control device controls said reversing device to reverse said function performed by said restriction device.

82. The apparatus according to claim 80, wherein said reversing device comprises hydraulic means including a valve for shifting the flow direction of a fluid in said hydraulic means.

83. The apparatus according to claim 80, wherein said reversing device comprises a mechanical reversing device.

84. The apparatus according to claim 83, wherein said mechanical reversing device comprises a gear box.

85. The apparatus according to claim 80, wherein said reversing device comprises a switch.

86. The apparatus according to claim 85, wherein said switch is operable by said released energy.

87. The apparatus according to claim 86, wherein said control device controls the operation of said switch by shifting polarity of said released energy.

88. The apparatus according to claim 86, wherein said switch comprises an electric switch and said control device releases electric energy from said external source of energy for the operation of said switch.

89. The apparatus according to claim 70, wherein said operation device comprises a motor, and said reversing device reverses said motor.

90. The apparatus according to claim 80, wherein said restriction device comprises hydraulic means and said operation device comprises a pump for pumping a fluid in said hydraulic means.

91. The apparatus according to claim 90, wherein said operation device comprises a motor for driving said pump.

92. The apparatus according to claim 91, wherein said operation device comprises a fluid conduit between said pump and said hydraulic means of said restriction device, and a reservoir for fluid, said reservoir forming part of said conduit.

93. The apparatus according to claim 92, wherein said hydraulic means, pump and conduit is devoid of any non-return valve.

94. The apparatus according to claim 93, wherein said reservoir forms a fluid chamber with a variable volume, and said pump distributes fluid from said chamber to said hydraulic means of said restriction device by reduction of the volume of said chamber and withdraws fluid from said hydraulic means to said chamber by expansion of the volume of said chamber.

95. The apparatus according to claim 1, further comprising at least one implanted sensor for sensing at least one physical parameter of the patient.

96. The apparatus according to claim 95, wherein said sensor comprises a pressure sensor for directly or indirectly sensing the pressure in said passageway.

97. The apparatus according to claim 95, wherein said control device controls said restriction device in response to signals from said sensor.

98. The apparatus according to claim 97, wherein said control device comprises an internal control unit adapted to be implanted in the patient, said internal control unit controlling said restriction device in response to signals from said sensor.

99. The apparatus according to claim 97, wherein said control device comprises an external control unit outside the patient's body, said external control unit controlling said restriction device in response to signals from said sensor.

100. The apparatus according to claim 99, wherein said external control unit stores information on said physical parameter sensed by said sensor and is manually operated to control said restriction device based on said stored information.

101. The apparatus according to claim 95, further comprising at least one sender adapted to be implanted in the patient for sending information on said physical parameter sensed by said sensor.

102. The apparatus according to claim 1, further comprising an external data communicator outside the patient's body and an internal data communicator adapted to be implanted in the patient for communicating with said external communicator, wherein said internal communicator feeds data related to the patient back to said external communicator or said external communicator feeds data to said internal communicator.

103. The apparatus according to claim 102, wherein said internal communicator feeds data related to said restriction device.

104. The apparatus according to claim 102, wherein said internal communicator feeds data related to at least one physical signal of patient.

105. The apparatus according to claim 1, wherein said restriction device controls the size of said stoma opening.

106. The apparatus according to claim 105, wherein said restriction device steplessly controls the size of said stoma opening.

107. The apparatus according to claim 1, wherein said control device releases wireless electric energy and said energy transfer device transfers said electric energy into kinetic energy for operation of said restriction device.

108. The apparatus according to claim 107, wherein said restriction device is directly operated with said kinetic energy, as said energy transfer device transfers said electric energy into said kinetic energy.

109. The apparatus according to claim 1, wherein said restriction device is non-inflatable.

110. The apparatus according to claim 1, wherein said control device releases energy for a determined time period.

111. The apparatus according to claim 1, wherein said control device releases energy in a determined number of energy pulses.

112. The apparatus according to claim 1, wherein said control device releases energy from said source of energy in a non-invasive manner.

113. The apparatus according to claim 1, wherein said control device comprises a wireless remote control transmitting at least one wireless control signal for controlling said restriction device.

114. The apparatus according to claim 113, wherein said remote control is capable of obtaining information on the condition of said restriction device and to control said restriction device in response to said information.

115. The apparatus according to claim 113, wherein said wireless remote control comprises at least one external signal transmitter or transceiver and at least one internal signal receiver or transceiver adapted to be implanted in the patient.

116. The apparatus according to claim 113, wherein said wireless remote control comprises at least one external signal receiver or transceiver and at least one internal signal transmitter or transceiver adapted to be implanted in the patient.

117. The apparatus according to claim 113, wherein said remote control is capable of sending information related to said restriction device from inside the patient's body to the outside thereof.

118. The apparatus according to claim 117, wherein said remote control controls said restriction device in response to said information.

119. The apparatus according to claim 113, wherein said remote control transmits a carrier signal for carrying said control signal.

120. The apparatus according to claim 119, wherein said carrier signal is frequency, amplitude or frequency and amplitude modulated.

121. The apparatus according to claim 119, wherein said carrier signal is digital, analog or digital and analog.

122. The apparatus according to claim 119, wherein said control signal used with said carrier signal is frequency, amplitude or frequency and amplitude modulated.

123. The apparatus according to claim 113, wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

124. The apparatus according to claim 113, wherein said control signal comprises an electric, magnetic or electric and magnetic field.

125. The apparatus according to claim 113, wherein said control signal is digital, analog or digital and analog.

126. The apparatus according to claim 125, wherein said remote control transmits an electromagnetic carrier wave signal for carrying said digital or analog control signal.

127. The apparatus according to claim 113, wherein said control signal is transmitted in pulses by said wireless remote control.

128. The apparatus according to claim 1, wherein said control device releases energy from said source of energy in a non-invasive manner.

129. The apparatus according to claim 1, wherein said control device releases magnetic energy.

130. The apparatus according to claim 1, wherein said control device releases electromagnetic energy.

131. The apparatus according to claim 1, wherein said control device releases kinetic energy.

132. The apparatus according to claim 1, wherein said control device releases thermal energy.

133. The apparatus according to claim 1, wherein said control device releases energy from said external source of energy in a mechanical manner.

134. The apparatus according to claim 1, wherein said control device releases non-magnetic energy.

135. The apparatus according to claim 1, wherein said control device releases non-electromagnetic energy.

136. The apparatus according to claim 1, wherein said control device releases non-kinetic energy.

137. The apparatus according to claim 1, wherein said control device releases non-thermal energy.

138. The apparatus according to claim 1, wherein said control device releases energy from said external source of energy in a non-mechanical manner.

139. A method of treating a human or animal suffering from morbid obesity, comprising:
(a) surgically implanting in the human or animal an operable restriction device engaging the human's or animal's stomach, or esophagus, to form an upper pouch of the stomach and a restricted stoma opening in the stomach or esophagus,
(b) providing a source of energy external to the patient's body,
(c) controlling the external source of energy from outside the patient's body to release wireless energy,
(d) transferring said wireless energy into a different form of energy usable by for operating said restriction device, and
(e) using said different form of energy for operating the restriction device to vary the restricted stoma opening.

140. A method according to claim 139, further comprising (e) implanting in the human or animal an operation device which can adjust the restricted stoma opening in response to supplied energy.

141. A method according to claim 140, further comprising (f) using the released wireless energy to activate the implanted operation device to vary the stoma opening.

142. A method according to claim 141 wherein (f) it may be practiced several times during the first year after the operation.

143. A method of treating a human or animal suffering from morbid obesity, comprising the steps of:
placing at least two laparoscopical trocars in the human's or animal's body,
inserting a dissecting tool through the trocars and dissecting an area of the stomach or esophagus,
placing an operable restriction device in the dissected area in engagement with the stomach or the esophagus to form a restricted stoma opening in the stomach or esophagus,
providing an external source of energy outside the human's or animal's body,
controlling said external source of energy from outside the patient's body to release wireless energy,
transferring said wireless energy into a different form of energy usable for operating said restriction device, and
using said different form of energy for operating said restriction device to vary the restricted stoma opening.

144. A method of treating a human or animal suffering from morbid obesity, comprising the steps of:
 placing at least two laparascopical trocars in the human's or animal's body,
 inserting a dissecting tool through the trocars and dissecting an area of the stomach or esophagus,
 implanting an operable restriction device in the dissected area in engagement with the stomach or the esophagus to form a restricted stoma opening in the stomach or esophagus,
 implanting an energy transfer device,
 providing an external source of energy,
 controlling the external source of energy to release wireless energy, and
 transferring the wireless energy by the energy transfer device into energy different than the wireless energy for operating the restriction device to vary the restricted stoma opening.

145. A method according to claim 144, further comprising implanting a stabilizer in the human or animal for stabilizing the energy transferred by the energy transfer device.

* * * * *